(12) United States Patent
Ahn

(10) Patent No.: US 11,759,248 B2
(45) Date of Patent: Sep. 19, 2023

(54) MEDICAL HANDPIECE HAVING HIGH FREQUENCY HEATING FUNCTION

(71) Applicant: AGNES MEDICAL CO., LTD, Seongnam-si (KR)

(72) Inventor: Gunyoung Ahn, Seongnam-si (KR)

(73) Assignee: AGNES MEDICAL CO., LTD., Seongnam-si (KR)

( * ) Notice: Subject to any disclaimer, the term of this patent is extended or adjusted under 35 U.S.C. 154(b) by 335 days.

(21) Appl. No.: 17/169,028

(22) Filed: Feb. 5, 2021

(65) Prior Publication Data
US 2022/0183740 A1 Jun. 16, 2022

(30) Foreign Application Priority Data
Dec. 16, 2020 (KR) .......... 10-2020-0176653

(51) Int. Cl.
*A61B 18/14* (2006.01)
*A61B 18/00* (2006.01)

(52) U.S. Cl.
CPC ...... *A61B 18/14* (2013.01); *A61B 2018/0047* (2013.01); *A61B 2018/00154* (2013.01);
(Continued)

(58) Field of Classification Search
CPC .......... A61B 18/14; A61B 2018/00154; A61B 2018/00202; A61B 2018/0047; A61B 2018/143; A61N 1/403
See application file for complete search history.

(56) References Cited

U.S. PATENT DOCUMENTS 6,743,211 B1 * 6/2004 Prausnitz ......... A61B 5/150083
604/173
8,540,705 B2 * 9/2013 Mehta ................ A61B 18/1477
606/41
(Continued)

FOREIGN PATENT DOCUMENTS

| JP | 2018-029892 A | 3/2018 |
| KR | 10-0943089 B1 | 2/2010 |
| KR | 10-2019-0084701 A | 7/2019 |

OTHER PUBLICATIONS

Korean Office Action for related KR Application No. 10-2020-0176653 dated Jan. 17, 2023 from Korean Intellectual Property Office.

*Primary Examiner* — Michael F Peffley
(74) *Attorney, Agent, or Firm* — Paratus Law Group, PLLC

(57) ABSTRACT

Disclosed is a medical handpiece having a high frequency heating function. The medical handpiece includes: a needle unit including a needle holder installed outside a distal portion of a handpiece body portion and needles configured to protrude forward from the needle holder; a high-frequency generator configured to apply a high-frequency current to the needle to generate heat when the distal end of the needle is inserted into the epidermal layer; a drug delivery unit installed to deliver a drug to the needle; and a skin expansion member including a guide main body installed to protrude outward of the handpiece body portion and a pair of rotational expansion plates configured to expand a skin in both directions while rotating about a hinge shaft on both sides of a distal portion of the guide main body.

8 Claims, 4 Drawing Sheets

(52) U.S. Cl.
CPC ............... *A61B 2018/00202* (2013.01); *A61B 2018/143* (2013.01)

(56) References Cited

U.S. PATENT DOCUMENTS

| | | | |
|---|---|---|---|
| 10,624,696 B2* | 4/2020 | Deem | A61B 18/18 |
| 11,097,100 B2* | 8/2021 | Seo | A61M 37/00 |
| 11,439,459 B2* | 9/2022 | Ko | A61N 1/08 |
| 2010/0217254 A1* | 8/2010 | Mehta | A61N 7/00 |
| | | | 606/41 |
| 2012/0158100 A1* | 6/2012 | Schomacker | A61B 18/1477 |
| | | | 607/101 |
| 2020/0093996 A1* | 3/2020 | An | A61N 1/0502 |
| 2022/0370731 A1* | 11/2022 | Park | A61B 18/1402 |

* cited by examiner

FIG. 3
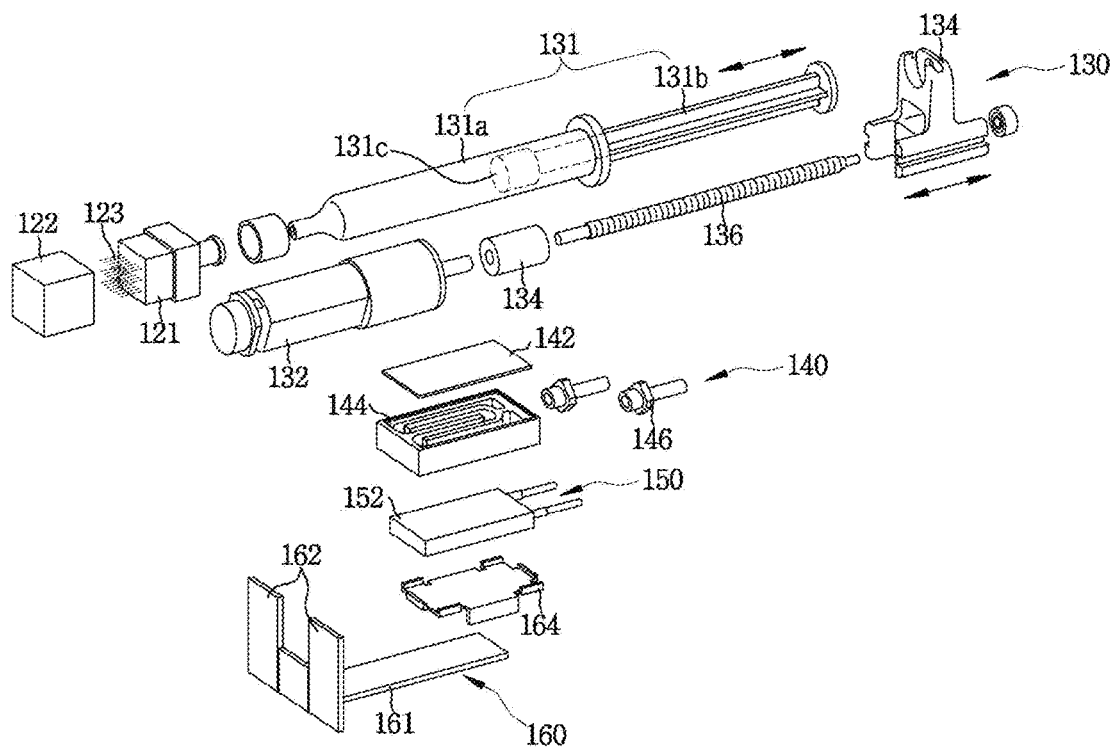
FIG. 4A  FIG. 4B  FIG. 4C  FIG. 4D
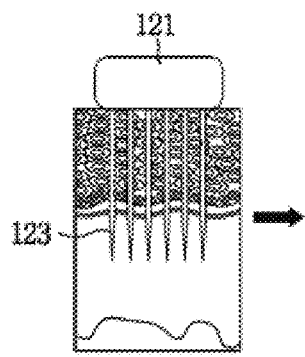 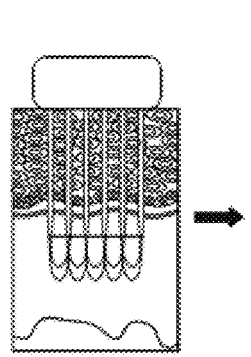 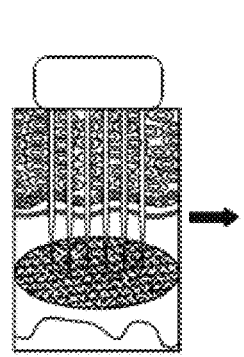 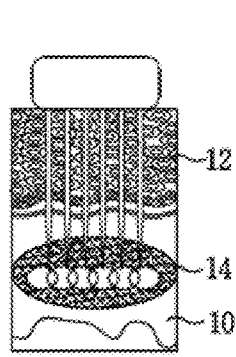

MEDICAL HANDPIECE HAVING HIGH FREQUENCY HEATING FUNCTION

CROSS-REFERENCE TO PRIOR APPLICATION

This application claims priority to Korean Patent Application No. 10-2020-0176653 (filed on Dec. 16, 2020), which is hereby incorporated by reference in its entirety.

BACKGROUND

The present disclosure relates to a treatment device, and more particularly, to a medical handpiece having a high frequency heating function capable of suppressing pain of a treatment subject and obtaining a continuous and fundamental skin treatment effect by using both high frequency and drugs.

In general, a high-frequency current refers to an alternating current of 100,000 Hz or more and has a short vibration width. Accordingly, in the high-frequency current, there is no electrochemical reaction or electrolysis phenomenon, and vibration current energy is converted into thermal energy only within a predetermined path.

In particular, when the high-frequency current energizes human tissues, since the high-frequency current has a very short vibration width, the high-frequency current rarely causes ionic motion and does not cause the electrochemical reaction or electrolysis phenomenon. When high-frequency electrical energy is applied to tissues, molecules constituting the tissue vibrate and rub against each other whenever a direction of a current changes, and thus generate bioheat.

In addition, unlike other currents, the high-frequency current can generate thermal energy without stimulating sensory and motor nerves and causing discomfort or muscle contraction in a human body, and this thermal energy can also enhance functions of cells and induce additional effects of increasing blood flow.

Accordingly, a high-frequency treatment device has been used for various treatment purposes such as skin care, hair promotion, or pain relief, as well as skin regeneration, lifting, suppression of melanin pigment secretion, or obesity treatment using a high-frequency current.

A general high-frequency treatment device includes a handpiece having a high-frequency electrode which is in contact with a treatment site of a skin and to which a high-frequency current is applied, and a main body having a high-frequency generator which receive power and supply a high-frequency current to the handpiece and a high-frequency operation controller which controls an operation of the high-frequency generator, in which the handpiece is electrically connected to the main body by a cable or the like.

The general high-frequency treatment device may cause some pain in a treatment subject, and there is some difficulty in continuous and fundamental skin treatment through only the high-frequency treatment device.

As an example of the high-frequency treatment device, Korean Patent No. 10-0943089 discloses a skin treatment device which has effects of preventing trauma and reducing pain on a skin surface when a conductive needle is inserted into a skin and maintains a constant depth of insertion of the needle.

The skin treatment device of Korean Patent No. 10-0943089 includes a plurality of needles coated with an insulating material except for a portion of a sharp end portion, a needle fixing unit which fixes the plurality of needles, a driver which directly or indirectly transmits a force to the needle fixing unit such that a plurality of needles fixed to the needle fixing unit are inserted into a skin, and an electromagnetic wave transmission unit which is electrically connected to the plurality of needles to transmit electromagnetic waves to the plurality of needles.

However, the high-frequency treatment device of the related art, such as the skin treatment device, is made for the purpose of high-frequency treatment only, does not perform a function of injecting a drug into the skin, and thus has a limitation in treatment effect.

SUMMARY

In view of the above, the present disclosure provides a medical handpiece having a high frequency heating function capable of improving therapeutic effects using high frequency and drug injection, suppressing occurrence of pain in a treatment subject during a treatment using high frequency, and improving therapeutic effects by expanding a skin when the high frequency and drug are applied.

The present disclosure also provides a medical handpiece having a high frequency heating function capable of effectively eliminating a back pressure when the back pressure occurs inside a syringe during a process of injecting drug into a skin so that the drug is precisely injected, and preventing air from being injected into the skin during the drug injection process.

In an aspect, there is provided a medical handpiece having a high frequency heating function, including: a handpiece body portion; a needle unit including a needle holder installed outside a distal portion of the handpiece body portion and having a hollow portion, and a plurality of needles configured to protrude forward from a distal portion of the needle holder, and having a hollow communicating with the hollow portion of the needle holder and a distal end inserted into a skin epidermal layer of a person to be treated; a high-frequency generator installed to electrically be coupled to the needle holder inside the handpiece body portion and configured to apply a high-frequency current to the needle to generate heat when the distal end of the needle is inserted into the epidermal layer; a drug delivery unit installed to communicate with the needle holder inside the handpiece body portion to deliver a drug to the needle; and a skin expansion member including a guide main body installed to protrude outward of the distal portion of the handpiece body portion and a pair of rotational expansion plates configured to expand a skin in both directions while rotating about a hinge shaft on both sides of a distal portion of the guide main body, and configured to pressure a skin layer of the person to be treated to which the plurality of needle are inserted to expand the skin layer in both directions.

The skin expansion member may be made of a thermally conductive metal material, and a cooling unit that is installed in connection with the guide main body to provide a cooling source to the guide main body and the rotational expansion plate may be installed inside the handpiece body portion.

The cooling unit may include a thermoelectric element having a cooling portion installed to be in contact with the guide main body and a heat dissipation module installed in connection with a heating unit of the thermoelectric element to receive heat.

The skin expansion member may further include an elastic body coupled to the hinge shaft to apply an elastic force to the rotational expansion plate downward so that a state where the rotational expansion plate is inclined at a certain angle with respect to the distal portion of the guide main body is maintained in an initial state in which no external force is applied.

The skin expansion member may further include a heat conduction elastic film made of a thermally conductive metal material attached to surfaces of the guide main body and the rotational expansion plate to transfer heat between the guide main body and the rotational expansion plate.

The heat conduction elastic film may be attached to a distal portion of the guide main body and a lower surface of the rotational plate in a state where a tensile force is applied to the heat conduction elastic film so that the rotational expansion plate being inclined at a certain angle with respect to the distal portion of the guide main body is maintained in a state where an external force is not applied to the rotational expansion plate.

In the medical handpiece having a high frequency heating function of the present disclosure which continuously improves the skin, the drug is injected after collagens of the skin epidermal layer are remodeled by using the high frequency. Accordingly, it is possible to increase persistence of the drug and increase improvement of the skin.

In the medical handpiece having a high frequency heating function of the present disclosure which continuously improves the skin, a skin surface layer which is a treatment target of a person to be treated is expanded and treated during the treatment, and thus it is possible to further improve therapeutic effects.

In the medical handpiece having a high frequency heating function of the present disclosure which continuously improves the skin, the skin surface layer which is the treatment target of the person to be treated is cooled and treated during the treatment, it is possible to relieve pain of the person to be treated.

In the medical handpiece having a high frequency heating function of the present disclosure which continuously improves the skin, when the drug is injected for a treatment, the piston of the syringe is moved backward stepwise. Accordingly, it is possible to effectively remove the back pressure generated during the injection of the drug and prevent air from being injected into the skin while the drug is injected.

BRIEF DESCRIPTION OF THE DRAWINGS

FIG. 3 is an exploded perspective view illustrating an internal configuration of the medical handpiece having a high frequency heating function illustrated in FIG. 1.

FIGS. 4A to 4I) are reference diagrams for guiding a skin treatment procedure of the medical handpiece having a high frequency heating function illustrated in FIG. 1.

DETAILED DESCRIPTION

Figure 1:
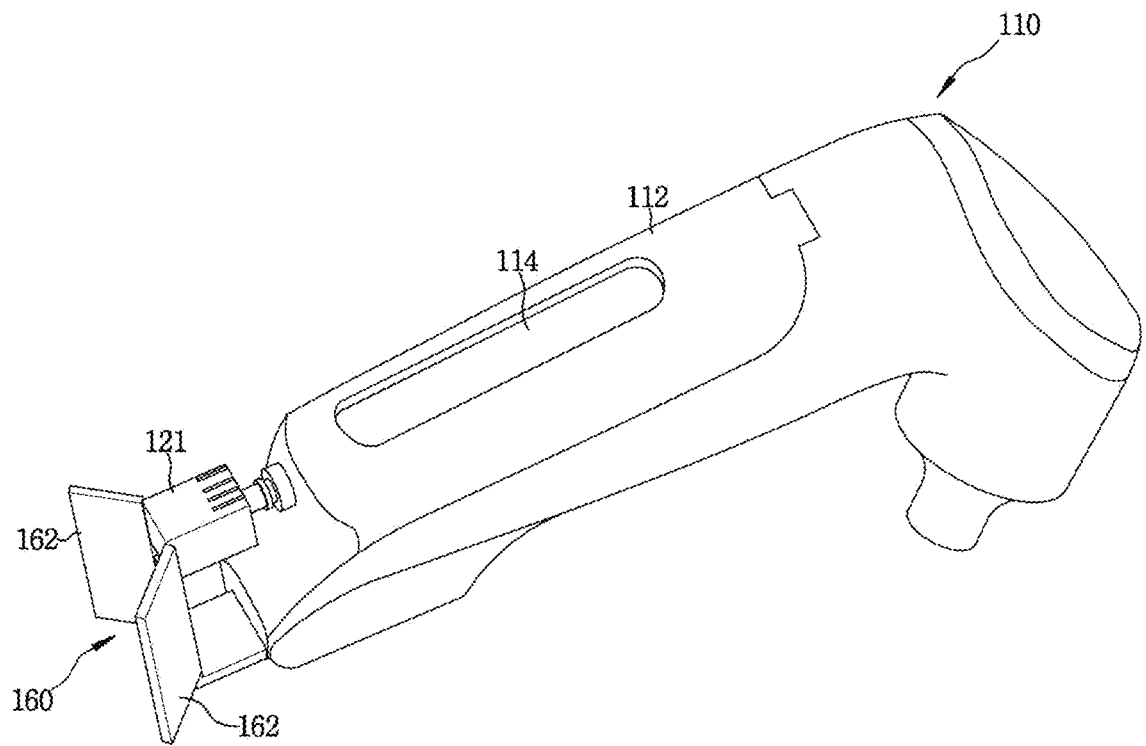
FIG. 1 is a perspective view of a medical handpiece having a high frequency heating function according to one embodiment of the present disclosure.
Figure 2:
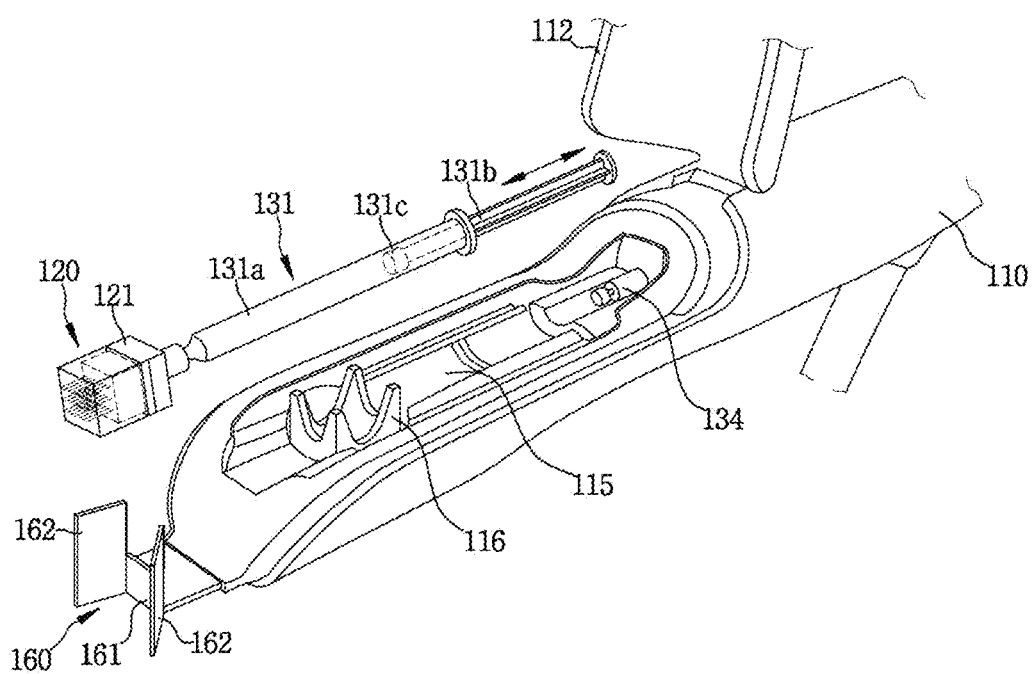
FIG. 2 is an exploded perspective view illustrating a partial configuration of the medical handpiece having a high frequency heating function illustrated in FIG. 1.
Figure 5A:
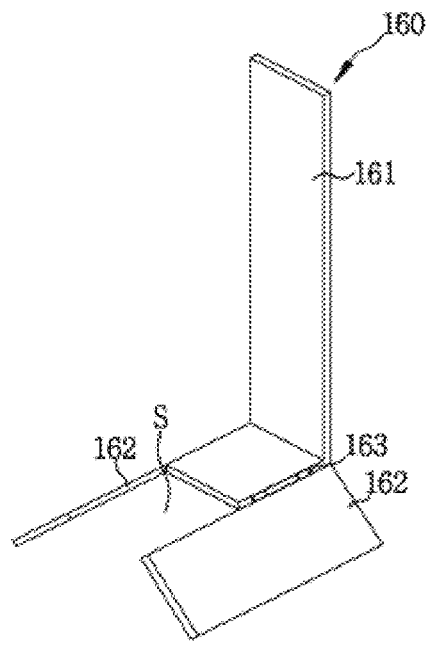
FIGS. 5A and 5B are perspective views illustrating an operation example of the medical handpiece having a high frequency heating function illustrated in FIG. 1.
Figure 5B:
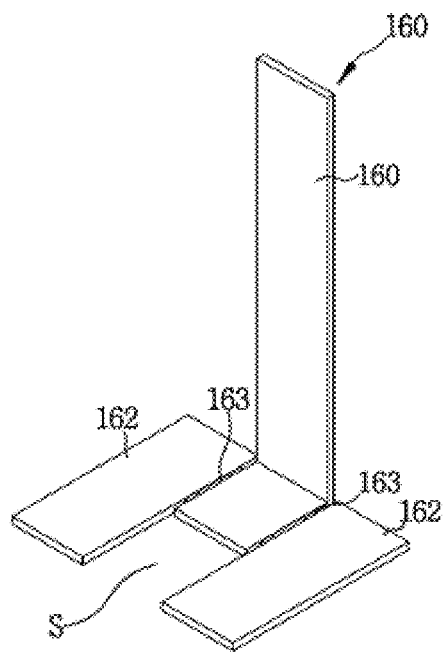
Figure 6A:
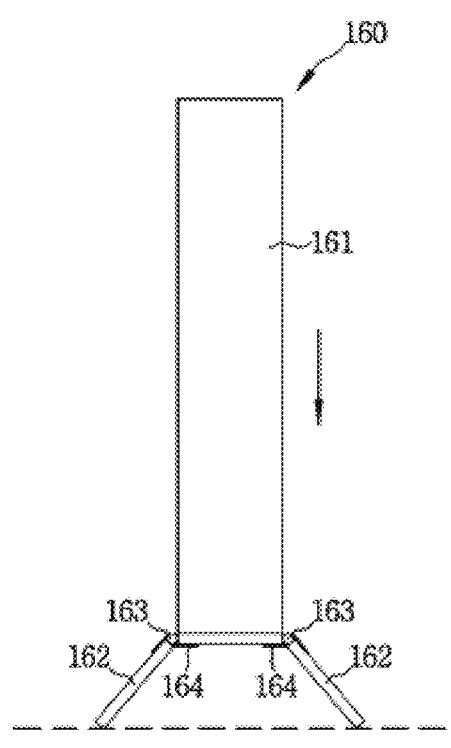
FIGS. 6A and 6B are front views illustrating an operation example of the medical handpiece having a high frequency heating function illustrated in FIG. 1.
Figure 6B:
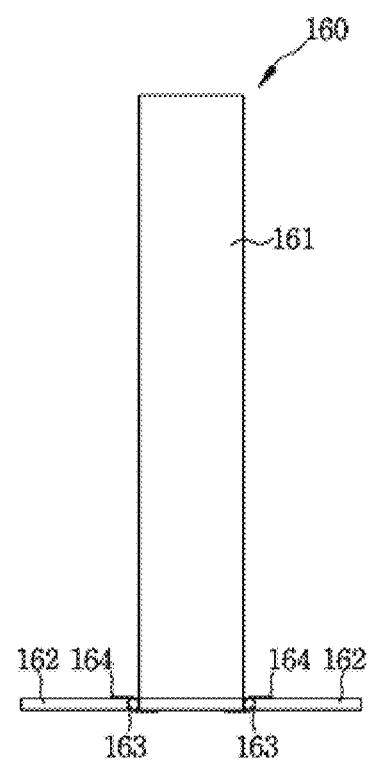

Before describing embodiments according to the present disclosure in detail, the present disclosure is not limited to configurations illustrated in the following detailed description or the accompanying drawings, and may be used or performed in various ways.

In addition, it should be understood that expressions or terms used herein are for the purpose of description only and should not be regarded as limiting.

That is, unless dictated or limited to represent something else, expressions such as "mounted", "installed", "connected", "coupled", "supported", "combined" used herein are used in a wide range of expressions including direct and indirect mountings, installations, connections, couplings, supports, and combinations. The expressions "connected", "coupled", and "combined" are not limited to physical or mechanical connections, couplings, or combinations.

In addition, in the present specification, terms indicating directions such as top, bottom, downward, upward, rear, bottom, front, or rear are used to describe the drawings, but these terms are used in directions (when viewed normally) relative to the drawings for convenience. Terms indicating the directions should not be taken as literally limiting or limiting the present disclosure in any form.

In addition, terms such as "first", "second", and "third" used in the present specification are for illustrative purposes only and should not be considered to mean relative importance.

Hereinafter, the embodiments of the present disclosure will be described in detail with reference to the accompanying drawings.

Referring to FIGS. 1 to 4D, a medical handpiece 100 having a high frequency heating function according to one embodiment of the present disclosure includes a handpiece body portion 110, a needle unit 120, a high-frequency generator, a drug delivery part 130, and a skin expansion member 160.

The handpiece body portion 110 is formed in a streamlined shape which is easy for a user to hold the medical handpiece 100 in his/her hands and perform treatment on a skin of a person to be treated, and one side of the handpiece body portion 110 includes a button (not illustrated) which controls an operation of the medical handpiece 100 such as operating or stopping the medical handpiece 100.

The high-frequency generator which applies a high frequency current to the needle unit 120 and the drug delivery unit 130 which supplies a drug to the needle unit 120 are installed in the handpiece body portion. In addition, a syringe installation groove 115 for detachably installing the syringe 131 constituting the drug delivery unit 130 is formed to be recessed in the handpiece body portion 110. A syringe holder 116 capable of pressing and supporting a cylinder 131a of the syringe 131 may be provided inside the syringe installation groove 115. The syringe installation groove 115 may be opened and closed by a handpiece cover 112 which is rotatably installed on the handpiece body portion 110. The handpiece cover 112 may include a transparent window 114 through which a drug state of the syringe 131 can be checked visually.

The high-frequency generator and the drug delivery unit 130 configured in the handpiece body unit 110 are coupled to an external control device by wire or wirelessly to receive a control signal. In addition, the handpiece body portion 110 includes various sensors capable of detecting state information of each component of the medical handpiece to transmit state information data of the medical handpiece to the control device or receive a control signal to control the operation of the medical handpiece from the control device.

The needle unit 120 includes a plurality of needles 123 having hollows therein and a needle holder 121 which fixedly supports the plurality of needles 123, includes hollow portions communicating with the hollows of the plurality of needles 123 therein, and is detachably provided in the handpiece body portion 110. In addition, the needle unit 120 includes a separate detachable needle cap 122 which protects the needles 123 from external contamination.

The needle holder 121 is electrically coupled to the high-frequency generator (not illustrated) in the handpiece body portion 110 to receive a high frequency current, and the hollow portion formed inside the needle holder 121 communicates with the syringe 131 of the drug delivery unit 130 to receive drugs.

The drug delivery unit 130 communicates with the needle holder 121 to deliver the drug to a skin epidermal layer of the person to be treated through the needles 123 inserted into the skin epidermal layer of the person to be treated, and is provided in the form of a syringe inside the handpiece body portion 110.

That is, as illustrated in FIG. 3, the drug deliver unit 130 includes the cylindrical cylinder 131a communicating with the needle holder 121, a piston 131b which is slidably installed in the cylinder 131a and presses the drug injected into the cylinder 131a to discharge the drug to the needle holder 121, the syringe 131 including a sealing material 131c which is provided on a distal end of the piston 131b and made of an elastic material, and a syringe driver which moves the piston 131b of the syringe 131 forward by the control signal applied from the control device to inject the drug. In this embodiment, the syringe driver includes a motor 132 which receives the control signal from a control device and is operated, a screw shaft 136 which is rotated by the motor 132, and a piston operation member 134 which includes a female screw (not illustrated) meshing with threads formed on an outer surface of the screw shaft 136, is slidably provided with respect to the handpiece body portion 110, and moves the piston 131b forward while sliding as the screw shaft 136 rotates.

The syringe driver is configured to control generation of a back pressure during drug injection.

The drug in the cylinder 131a of the syringe 131 is a formulation having a high viscosity, and when the drug is injected by pushing the piston 131b forward using the syringe driver, the sealing material 131c at the distal end of the piston 131b is partially compressed by a pressure caused by the viscosity of the drug. Therefore, while the sealing material 131c made of an elastic material such as rubber is restored to an original state thereof after the compression, an amount of the discharged drug initially has a high discharge value, but has a slow discharge value in a late period. Therefore, in order to inject a desired dose, it takes a very long time before the drug is discharged.

For this reason, in order to deliver drugs quickly, an output of the motor 132 is controlled to be about 20 to 40% (low capacity is 20% and high capacity is 40% depending on the capacity) higher than a target value considering the compression of the sealing material 131c, a movement distance of the piston operation member 134 increases by 20 to 40%, and thus a target amount of drug can be injected during a predetermined time. For example, when the volume of the drug to be injected is 100, the output of the motor is controlled so that an amount of change in an internal volume of the cylinder 131a by the movement of the piston 131b of the syringe 131 is 120 to 140 instead of 100.

In this case, if the motor 132 is controlled to a value increased from the target value to move the piston 131b forward, as described above, the sealing material 131c is compressed and the back pressure is generated by the viscosity of the drug. Accordingly, in order to eliminate the back pressure and compression, the piston 131b is moved backward by a certain distance. In this case, the total backward-movement distance is equal to the increase in the above-described forward-movement distance. The backward-movement control of the piston 131b is not performed at once, but is divided into several stages. For example, if the movement distance of the piston operation member 134 is increased by 40% from 100, which is the target value (movement distance corresponding to the volume of the drug), the piston 131b is compressed and cannot move by 140 and moves approximately 80 to 90. In this case, if the motor 132 is controlled in a reverse direction and the piston 131b is moved backward by 20, which is 50% of the total increase in the forward operation, an internal pressure of the syringe 131 rapidly decreases and the drug having a target amount can be discharged. However, since the drug in the needle 123 is condensed at a tip of the needle 123 or is partially coming out due to an error, the piston is further moved backward by 15 to relieve the pressure remaining inside the syringe 131, and thereafter, the piston moves backward by 5 again to stop the drug at an end of the needle 123. That is, 50% of the total target backward movement during the backward movement of the piston 131b is achieved when an injection similar to an injection amount of a first target drug is made, and a second 30% is a process for removing the internal pressure of the syringe 131, and a third 20% is a process of stopping the discharged drug at the end of the needle 123.

If the piston 131b is fully moved backward once after moving forward, since there is no consideration of the process of returning to the original state after the compression of the sealing material 131c which continues during the backward movement, the internal pressure of the syringe 131 is removed, but air is injected into the needle 123 and a portion of the needle holder 121 after the operation ends, and thus air may be partially injected into the skin when the drug is injected later. However, as described above, when the piston unit 131b is moved backward by controlling the motor 132 in the reverse direction, the backward movement process is controlled to be divided into at least three steps, and thus the back pressure can be eliminated and the injection of air can be prevented.

Meanwhile, the skin expansion member 160 expands a skin layer which is a treatment target of the person to be treated in both directions so that the needle 123 is completely inserted into the epidermal layer of the person to be treated without a separate negative pressure structure, provides a cooling source to the skin layer which is the treatment target of the person to be treated to cool the surface layer of the skin, and thus relieves pain of the person to be treated caused by the treatment.

In order to provide the cooling source to the skin layer through the skin expansion member 160, as illustrated in FIG. 3, the skin expansion member 160 is made of a metal material having excellent thermal conductivity, and as a cooling unit for providing the cooling source to the skin expansion member 160, a thermoelectric element 150 and a heat dissipation module 140 which is installed in connection with a heating unit of the thermoelectric element 150 to receive heat are installed in the handpiece body portion 110. The skin expansion member 160 is installed in connection with a cooling unit of the thermoelectric element 150 via a heat transfer bracket 164 made of a thermally conductive metal material, and thus, heat of the skin expansion member 160 is dissipated and the skin expansion member 160 is cooled. Therefore, when a drug is injected through the needle unit 120 and a high frequency is generated to perform a treatment, the skin expansion member 160 cools the skin layer to relieve pain while preventing skin burns due to the high frequency.

FIGS. 5A to 6B, the skin expansion member 160 is made of a metal material having excellent thermal conductivity, and includes an L-shaped guide main body 161 which is installed to protrude from a distal portion of the handpiece body portion 110, and a pair of rotational expansion plates 162 which expands the skin in both directions while rotating about hinge shafts 163 on both sides of a distal portion of the guide main body 161. A downward elastic force is applied to the rotational expansion plate 162 by an elastic body 164. Accordingly, in an initial state in which no external force is applied, a state where the rotational expansion plate 162 is inclined at a certain angle with respect to the distal portion of the guide main body 161 is maintained. When an operator presses the distal portion of the skin expansion member 160 on the skin of the person to be treated, the rotational expansion plate 162 overcomes the elastic force of the elastic body 164 and is expanded while rotating upward about the hinge axis 163 (refer to FIGS. 5B and 6B). Accordingly, the skin is pushed in both directions and expanded. In this case, the skin located in a space between the pair of rotational expansion plates 162 is pressed by the rotational expansion plate 162 and raised slightly upward, and the needle 123 can be easily inserted to a certain depth.

The rotational expansion plate 162 is formed in a flat plate having a length slightly longer than that of a portion bent at a right angle to the distal portion of the guide main body 161, and a space in which the needle 123 is located is formed between the pair of rotational expansion boards 162 and the distal end of the guide main body 161.

In addition, the rotational expansion plate 162 has an initial state inclined at a certain angle with respect to the distal portion of the guide main body 161 by the elastic body 164, and thus, the rotational expansion plate 162 rotates in a state where the elastic force is applied to the rotational expansion plate 162 when the rotation expansion plate 162 comes into close contact with the skin of the person to be treated. Accordingly, the skin is expanded to both sides.

Figure 7A:
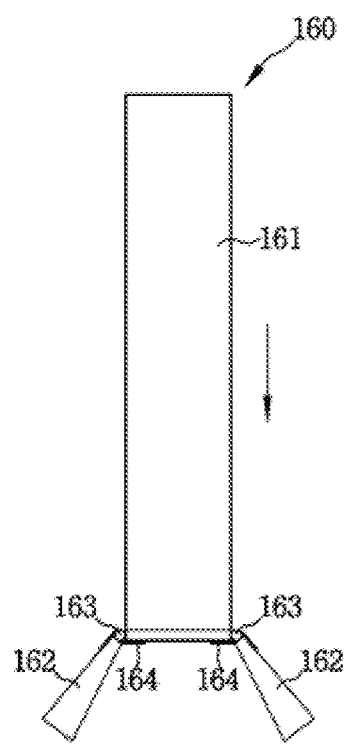
FIGS. 7A and 7B are corresponding views of FIGS. 6A and 6B and front views illustrating another embodiment of a skin expansion member constituting the medical handpiece having a high frequency heating function according to the present disclosure.
Figure 7B:
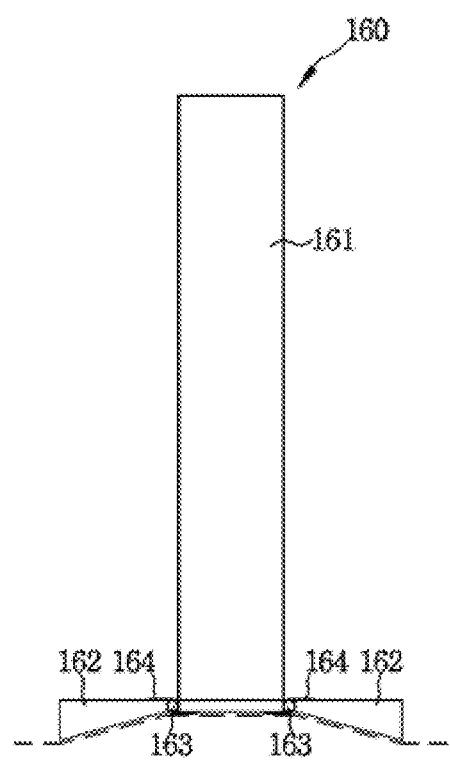

As illustrated in FIGS. 7A and 7B, a thickness of the rotational expansion plate 162 may increase from an inner portion (portion coupled to the hinge shaft) to an outer portion so that the skin can be more smoothly expanded by the rotational expansion plate 162 of the skin expansion member 160.

Figure 8:
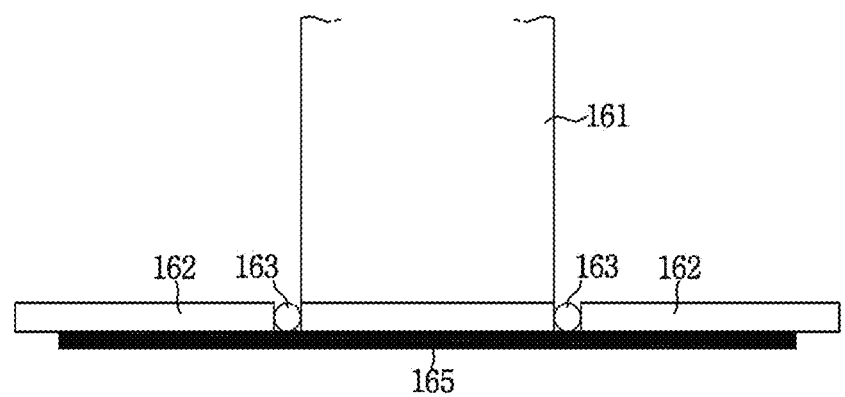
FIG. 8 is a cross-sectional view of a main portion illustrating still another embodiment of the skin expansion member constituting the medical handpiece having a high frequency heating function according to the present disclosure.

In addition, as illustrated in FIG. 8, in order to facilitate heat transfer between the guide main body 161 of the skin expansion member 160 and the rotational expansion plate 162 to increase cooling effects, a heat conduction elastic film 165 made of a metal material having excellent thermal conductivity may be attached. In a case where a tensile force is applied to the heat conduction elastic film 165 and the heat conduction elastic film 165 is attached to the distal portion of the guide main body 161 and a lower surface of the rotational expansion plate 162, even though the separate elastic body 164 (refer to FIGS. 6A and 6B) is not installed in the hinge shaft 163 as in the above-described embodiment, when the external force is removed from the rotation expansion plate 162, the rotational expansion plate 162 can be automatically returned to the initial state (states of FIGS. 5A and 6A).

Hereinafter, an operation of the medical handpiece having a high frequency heating function will be described in detail.

First, as illustrated in FIGS. 4A and 4B, when the needles 123 are inserted into the skin epidermal layer of the person to be treated and then high frequency is applied, collagens in the skin epidermal layer are remodeled. Moreover, when the high frequency is applied, the skin epidermal layer suffers a weak electric burn.

Subsequently, as illustrated in FIGS. 4C and 4D, the drug is delivered through the drug delivery unit 130. In this way, when the collagens in the skin epidermal layer are remodeled through high frequency and a weak electrical burn is applied, and then the drug is delivered, persistence of the injected drug increases. Accordingly, skin elasticity increases, pores and fine lines are improved, weak electrical burns in the skin tissue inhibits absorption of hyaluronic acid in the injected drug, and thus the duration of the effect that the skin becomes transparent by the drug increases.

When the high frequency and drug are applied to the skin epidermal layer to perform the treatment, the needle 123 can be inserted into the skin epidermal layer of the person to be treated while the skin is expanded to both sides by the skin expansion members 160, and thus the needle 123 can be easily inserted into the skin epidermal layer. In addition, since the skin epidermal layer can be cooled through the skin expansion member 160, pain can be relieved in a treatment process and skin burns caused by high frequency can be prevented.

Heretofore, preferred embodiments of the present disclosure are described. However, the present disclosure can use various changes, modifications, and equivalents. It is clear that the present disclosure can be applied equally by appropriately modifying the embodiments. Therefore, the above description does not limit a scope of the present disclosure determined by the limits of the following claims.

[Detailed Description of Main Elements]

| | |
|---|---|
| 100: treatment device | 110: handpiece body portion |
| 112: handpiece cover | 114: window |
| 115: syringe installation groove | 116: syringe holder |
| 120: needle unit | 121: needle holder |
| 122: needle cap | 123: needle |
| 130: drug delivery unit | 131: syringe |
| 131a: cylinder | 131b: piston |
| 132: motor | 134: piston operation member |
| 136: screw shaft | 140: heat dissipation module |
| 150: thermoelectric element | 160: skin expansion member |
| 161: guide main body | 162: rotational expansion plate |
| 163: hinge shaft | 164: elastic body |
| 165: heat conduction elastic film | |

What is claimed is:

1. A medical handpiece having a high frequency heating function, comprising:

a handpiece body portion;

a needle unit including a needle holder installed outside a distal portion of the handpiece body portion and having a hollow portion, and a plurality of needles configured to protrude forward from a distal portion of the needle holder, wherein each needle has a hollow interior communicating with the hollow portion of the needle holder and a distal end configured to be inserted into a skin epidermal layer of a person to be treated;

a high-frequency generator installed to electrically be coupled to the needle holder inside the handpiece body portion and configured to apply a high-frequency current to the plurality of needles to generate heat when the distal end of each needle is inserted into the epidermal layer;

a drug delivery unit installed to communicate with the needle holder inside the handpiece body portion to deliver a drug to the plurality of needles; and a skin expansion member including a guide main body installed to protrude outward of the distal portion of the handpiece body portion and a pair of rotational expansion plates configured to expand a skin in both directions while rotating about a hinge shaft on both sides of a distal portion of the guide main body, and configured to pressure a skin layer of the person to be treated to which the plurality of needles are inserted to expand the skin layer in both directions, wherein the skin expansion member further includes a heat conduction elastic film made of a thermally conductive metal material attached to surfaces of the guide main body and the rotational expansion plate to transfer heat between the guide main body and the rotational expansion plate.

2. The medical handpiece having a high frequency heating function of claim 1, wherein the skin expansion member is made of a thermally conductive metal material, and a cooling unit that is installed in connection with the guide main body to provide a cooling source to the guide main body and the rotational expansion plate is installed inside the handpiece body portion.

3. The medical handpiece having a high frequency heating function of claim 2, wherein the cooling unit includes a thermoelectric element having a cooling portion installed to be in contact with the guide main body and a heat dissipation module installed in connection with a heating unit of the thermoelectric element to receive heat.

4. The medical handpiece having a high frequency heating function of claim 1, wherein the skin expansion member further includes an elastic body coupled to the hinge shaft to apply an elastic force to the rotational expansion plate downward so that a state where the rotational expansion plate is inclined at a certain angle with respect to the distal portion of the guide main body is maintained in an initial state in which no external force is applied.

5. The medical handpiece having a high frequency heating function of claim 1, the heat conduction elastic film is attached to a distal portion of the guide main body and a lower surface of the rotational plate in a state where a tensile force is applied to the heat conduction elastic film so that the rotational expansion plate being inclined at a certain angle with respect to the distal portion of the guide main body is maintained in a state where an external force is not applied to the rotational expansion plate.

6. The medical handpiece having a high frequency heating function of claim 1, wherein the drug delivery unit includes a syringe having a tubular cylinder communicating with the needle holder, a piston which is installed slidable in the cylinder and pressures the drug injected into the cylinder to discharge the drug to the needle holder, and a sealing material made of an elastic material installed on a distal end of the piston, and a syringe driver having a motor configured to a control signal applied to a control device of the medical handpiece having a high frequency heating function, and configured to move the piston of the syringe by an operation of the motor to inject the drug.

7. A medical handpiece having a high frequency heating function, comprising:

a handpiece body portion;

a needle unit including a needle holder installed outside a distal portion of the handpiece body portion and having a hollow portion, and a plurality of needles configured to protrude forward from a distal portion of the needle holder, wherein each needle has a hollow interior communicating with the hollow portion of the needle holder and a distal end configured to be inserted into a skin epidermal layer of a person to be treated;

a high-frequency generator installed to electrically be coupled to the needle holder inside the handpiece body portion and configured to apply a high-frequency current to the plurality of needles to generate heat when the distal end of each needle is inserted into the epidermal layer;

a drug delivery unit installed to communicate with the needle holder inside the handpiece body portion to deliver a drug to the plurality of needles; and a skin expansion member including a guide main body installed to protrude outward of the distal portion of the handpiece body portion and a pair of rotational expansion plates configured to expand a skin in both directions while rotating about a hinge shaft on both sides of a distal portion of the guide main body, and configured to pressure a skin layer of the person to be treated to which the plurality of needles are inserted to expand the skin layer in both directions, wherein the drug delivery unit includes:

a syringe having a tubular cylinder communicating with the needle holder, a piston which is installed slidable in the cylinder and pressures the drug injected into the cylinder to discharge the drug to the needle holder, and a sealing material made of an elastic material installed on a distal end of the piston, and a syringe driver having a motor configured to a control signal applied to a control device of the medical handpiece having a high frequency heating function, and configured to move the piston of the syringe by an operation of the motor to inject the drug, wherein the syringe driver controls an output of the motor and moves the piston forward so that an amount of change in a volume inside the cylinder by a movement of the piston increases by a predetermined amount more than a volume of the drug to be injected into the skin, and operates the motor in a reverse direction to move the piston backward by a predetermined distance when the piston moves forward by a predetermined distance to eliminate a back pressure.

8. The medical handpiece having a high frequency heating function of claim 7, a process in which the syringe driver eliminates the back pressure is a process of operating the motor in the reverse direction stepwise over at least three steps so that the piston moves backward stepwise by a predetermined distance.

* * * * *